United States Patent
Richardson

(10) Patent No.: US 10,376,660 B2
(45) Date of Patent: *Aug. 13, 2019

(54) DRY POWDER INHALATION DEVICE

(71) Applicant: Concentrx Pharmaceuticals, Inc., Durham, NC (US)

(72) Inventor: Eric Carl Richardson, Cave Creek, AZ (US)

(73) Assignee: Concentrx Pharmaceuticals, Inc., Durham, NC (US)

( * ) Notice: Subject to any disclaimer, the term of this patent is extended or adjusted under 35 U.S.C. 154(b) by 292 days.

This patent is subject to a terminal disclaimer.

(21) Appl. No.: 15/265,428

(22) Filed: Sep. 14, 2016

(65) Prior Publication Data

US 2017/0000960 A1    Jan. 5, 2017

Related U.S. Application Data

(63) Continuation of application No. 14/343,498, filed as application No. PCT/US2012/054325 on Sep. 7, 2012, now Pat. No. 9,446,209.

(Continued)

(51) Int. Cl.
*A61M 15/00* (2006.01)

(52) U.S. Cl.
CPC ...... *A61M 15/0008* (2014.02); *A61M 15/002* (2014.02); *A61M 15/0021* (2014.02);
(Continued)

(58) Field of Classification Search
CPC .......... A61M 15/0001; A61M 15/0005; A61M 15/002; A61M 15/0028; A61M 15/0043;
(Continued)

(56) References Cited

U.S. PATENT DOCUMENTS 4,206,758 A    6/1980   Hallworth et al.
4,841,964 A *  6/1989   Hurka ............... A61M 15/0028
                                                  128/203.15

(Continued)

FOREIGN PATENT DOCUMENTS

CN    1192702 A     9/1998
CN    101795723 A   8/2010

(Continued)

OTHER PUBLICATIONS

PCT Search Report from corresponding PCT Application No. PCT/US2012/054325.

(Continued)

*Primary Examiner* — Michael J Tsai

(57) ABSTRACT

Taught herein is a disposable breath actuated dry powder drug inhalation device having a powderized drug storage chamber with integral toroidal geometry and air flow pathways for entraining and breaking up powder aggregates prior to delivery to the patient. The toroidal chamber is fluidly connected by one or more air inlets directed in a non-tangent manner toward the powder to loft and set up an irregular-rotational flow pattern. Also, in fluid connection with the toroidal chamber is a centrally or near centrally located air and powder outlet consisting of one or more holes forming a grid in fluid connection with a channel providing a passageway for powder flow to the patient.

18 Claims, 18 Drawing Sheets

Related U.S. Application Data

(60) Provisional application No. 61/573,496, filed on Sep. 7, 2011.

(52) U.S. Cl.
CPC .... *A61M 15/0028* (2013.01); *A61M 15/0043* (2014.02); *A61M 15/0091* (2013.01); A61M 2202/064 (2013.01); A61M 2206/16 (2013.01); A61M 2207/00 (2013.01); A61M 2207/10 (2013.01); A61M 2209/06 (2013.01)

(58) Field of Classification Search
CPC .......... A61M 15/0061; A61M 15/0063; A61M 15/0086; A61M 2202/064
See application file for complete search history.

(56) References Cited

U.S. PATENT DOCUMENTS

| | | | |
|---|---|---|---|
| 5,239,991 A | 8/1993 | Chawla et al. | |
| 5,239,993 A | 8/1993 | Evans | |
| 5,533,505 A | 7/1996 | Kallstrand et al. | |
| 5,660,169 A | 8/1997 | Kallstrand et al. | |
| 5,918,594 A | 7/1999 | Asking et al. | |
| 6,102,035 A | 8/2000 | Asking et al. | |
| 6,105,574 A | 8/2000 | Jahnsson | |
| 6,286,507 B1* | 9/2001 | Jahnsson ........... | A61M 15/0028 128/203.15 |
| 6,427,688 B1 | 8/2002 | Ligotke et al. | |
| 6,715,486 B2 | 4/2004 | Gieschen et al. | |
| 6,971,384 B2 | 12/2005 | Gieschen et al. | |
| 7,069,929 B2 | 7/2006 | Young et al. | |
| 7,143,765 B2 | 12/2006 | Asking et al. | |
| 7,322,353 B2 | 1/2008 | Young et al. | |
| 7,322,354 B2 | 1/2008 | Young et al. | |
| 7,434,579 B2 | 10/2008 | Young et al. | |
| 7,533,668 B1* | 5/2009 | Widerstrom ...... | A61M 15/0028 128/203.15 |
| 7,661,425 B2 | 2/2010 | Keldmann et al. | |
| 7,861,712 B2 | 1/2011 | Jones et al. | |
| 7,958,890 B2 | 6/2011 | Gieschen et al. | |
| 8,550,074 B2 | 10/2013 | Jones et al. | |
| 9,446,209 B2 | 9/2016 | Richardson | |
| 2001/0027790 A1 | 10/2001 | Gieschen et al. | |
| 2002/0092523 A1* | 7/2002 | Connelly ........... | A61M 15/0028 128/203.15 |
| 2002/0108611 A1 | 8/2002 | Johnston et al. | |
| 2004/0065329 A1 | 4/2004 | Geist | |
| 2004/0168687 A1 | 9/2004 | Asking et al. | |
| 2004/0200475 A1 | 10/2004 | Koane et al. | |
| 2005/0048003 A1 | 3/2005 | Ohki et al. | |
| 2005/0081851 A1 | 4/2005 | Young et al. | |
| 2005/0118111 A1 | 6/2005 | Goldemann | |
| 2005/0252510 A1 | 11/2005 | Young et al. | |
| 2006/0237010 A1* | 10/2006 | De Boer ........... | A61M 15/0045 128/203.15 |
| 2007/0081948 A1 | 4/2007 | Morton et al. | |
| 2007/0151562 A1 | 7/2007 | Jones et al. | |
| 2008/0173302 A1 | 7/2008 | Mecikalski | |
| 2008/0190424 A1* | 8/2008 | Lucking ............. | A61K 9/0075 128/203.15 |
| 2008/0314384 A1 | 12/2008 | Harris et al. | |
| 2009/0013994 A1 | 1/2009 | Jones et al. | |
| 2009/0084379 A1 | 4/2009 | Goeckner | |
| 2009/0223516 A1 | 9/2009 | Connelly et al. | |
| 2009/0235930 A1 | 9/2009 | Young et al. | |
| 2009/0235931 A1 | 9/2009 | Young et al. | |
| 2009/0250058 A1* | 10/2009 | Lastow ............. | A61M 15/0028 128/203.15 |
| 2009/0308391 A1 | 12/2009 | Smutney et al. | |
| 2010/0000531 A1 | 1/2010 | Smith et al. | |
| 2010/0059049 A1 | 3/2010 | Genosar | |
| 2010/0139655 A1 | 6/2010 | Genosar et al. | |
| 2010/0181387 A1 | 7/2010 | Zaffaroni | |
| 2010/0212667 A1 | 8/2010 | Smith et al. | |
| 2011/0061653 A1 | 3/2011 | Von Schuckmann | |
| 2011/0192397 A1 | 8/2011 | Saskar et al. | |
| 2012/0132204 A1 | 5/2012 | Lucking et al. | |
| 2013/0008442 A1 | 1/2013 | Jones et al. | |
| 2013/0025593 A1 | 1/2013 | Thirumalai Anandampillai | |
| 2013/0061851 A1 | 3/2013 | Jones et al. | |
| 2013/0199527 A1 | 8/2013 | Smutney et al. | |
| 2013/0291865 A1 | 11/2013 | Jones et al. | |
| 2014/0083423 A1* | 3/2014 | Jung ................. | A61M 15/0028 128/203.21 |
| 2018/0280639 A1 | 10/2018 | Richardson | |

FOREIGN PATENT DOCUMENTS

| | | |
|---|---|---|
| CN | 107106795 A | 8/2017 |
| DE | 10027639 A1 | 12/2001 |
| WO | WO9204928 A2 | 4/1992 |
| WO | WO1992004928 A2 | 4/1992 |
| WO | WO199413348 A1 | 6/1994 |
| WO | WO9419041 A1 | 9/1994 |
| WO | WO9834661 A1 | 8/1998 |
| WO | WO2000/53248 A1 | 9/2000 |
| WO | WO2003/000325 A1 | 1/2003 |
| WO | WO2003/103563 A2 | 12/2003 |
| WO | WO2008/042951 A2 | 4/2008 |
| WO | WO2009/009013 A2 | 1/2009 |
| WO | WO2009/121020 A1 | 10/2009 |
| WO | WO2009/133555 A1 | 11/2009 |
| WO | WO2012/088585 A1 | 7/2012 |

OTHER PUBLICATIONS

European Search Report from corresponding European application No. EP/12830544.
Office Action for Chinese Patent Application No. 201280054580.1, dated Jul. 28, 2015.
Office Action for Chinese Patent Application No. 201280054580.1, dated Mar. 31, 2016.
Office Action for U.S. Appl. No. 14/343,498, dated Jun. 21, 2016.
Chrystyn, H. The Diskus: A review of its position among dry powder inhaler devices. International Journal of Clinical Practice, Jun. 2007, 61, 6, pp. 1022-1036. 15 pages.
Office Action for Canadian Patent Application No. 2,846,899, dated Jun. 22, 2018.
International Search Report for PCT Application No. PCT/US2018/024882, dated Jun. 25, 2018.
First Office Action for Chinese Patent Application No. 201611041479.9, dated Mar. 25, 2019.

* cited by examiner

FRONT VIEW

TOP VIEW

SIDE VIEW

BOTTOM VIEW

REAR VIEW

TOP VIEW

SECTION 15B-15B

TOP VIEW

SECTION 16B-16B

Section 21B-21B

Section 21C-21C

DRY POWDER INHALATION DEVICE

CROSS-REFERENCE TO RELATED APPLICATIONS

This application is a continuation of U.S. patent application Ser. No. 14/343,498, entitled "Dry Powder Inhalation Device," filed Mar. 7, 2014, which is a national stage filing under 35 U.S.C. § 371 of International Patent Application No. PCT/US2012/054325, entitled "Dry Powder Inhalation Device," filed Sep. 7, 2012, which claims priority to U.S. Provisional Application Ser. No. 61/573,496, entitled "Dry Powder Inhalation Device," filed Sep. 7, 2011, each of which is incorporated herein by reference in its entirety.

COPYRIGHT NOTICE

A portion of the disclosure of this patent contains material that is subject to copyright protection. The copy right owner has no objection to the reproduction by anyone of the patent document or the patent disclosure as it appears in the Patent and Trademark Office patent files or records, but otherwise reserves all copyright rights whatsoever.

BACKGROUND

Field of the Invention

The present invention relates to a dry powder inhalation device for the inhalation of pharmaceutical or nutraceutical compounds including excipients in dry powder form. More particularly, it relates to a dry powder inhalation device having a toroidal chamber for uniform particle size delivery to a patient.

Description of Related Art

Pressurized metered dose inhalation devices (pMDI) are well-known for delivering drugs to patients by way of their lungs. pMDI's are comprised of a pressurized propellant canister with a metering valve housed in a molded actuator body with integral mouthpiece. This type of inhalation device presents drug delivery challenges to patients, requiring significant force to actuate with inhalation and timing coordination to effectively receive the drug. pMDI's containing suspended drug formulations also have to be shaken properly by the patient prior to actuating to receive an effective dose of the drug. These relatively complicated devices also require priming due to low drug content in initial doses and can require cleaning by the patient. In some devices, an additional spacer apparatus is prescribed along with the pMDI to compensate for the timing coordination issue although the downside for the patient has to pay for, clean, store and transport the bulky spacer apparatus. While many patients are experienced operating pMDI's or pMDI's with spacers, new patients have to go through the relatively significant learning curve to operate these devices properly.

Dry powder inhalation devices (DPI) are also well-known for delivering powderized drug to the lungs. DPI technologies are either active involving external energy to break-up and aerosolize particles or, passive utilizing the patient's inspiratory energy to entrain and deliver the powder to the lungs. Some DPI technologies integrate electronics while others are fully mechanical. The powder drug storage formats are normally reservoir, individually pre-metered doses or capsule based systems. Drug formulations delivered by these devices involve in some devices innovative engineered drug particles but in most devices deliver a conventional blend of sized active pharmaceutical ingredient(s) (API) plus sized lactose monohydrate used as a bulking agent to aid in the powder filling process and as carrier particles to aid in delivery of the active pharmaceutical ingredient(s) to the patient. These API-lactose monohydrate blends among others require a means to break-up aggregates formed by attractive forces holding them together.

Nebulizers are well known for delivering drugs in solution to the lung. While these drug delivery systems are effective for patients lacking the inhalation capability or coordination to operate some hand held inhalation devices, they are large equipment requiring an electrical power source, cleaning and maintenance. Administration of nebulizer drugs involves significant time and effort; transporting, setting up electrically, loading individual nebules, assembling the patient interface mouthpiece and delivering doses to the patient.

Inhalation therapies currently being administered in institutional settings are either multidose pMDI, multi-dose DPI's or nebulizer, all of which demand substantial attention of health care providers to administer. All current options require substantial effort from the nurse or respiratory therapist to administer, track doses and maintain to meet the needs of the patient. Current options available in the institutional setting require the in-house pharmacy to dispense multi-dose devices that in most devices contain an inappropriate number of doses relative to the patient's stay and disposal of unused doses when patients are released. Additionally, multi-dose inhalation devices requiring repeated handling over multiple days in these settings increase the chance of viral and bacterial transmission from person to device to person within the environment. Thus, the complexities associated with the currently available inhalation devices result in considerable cost impact to the healthcare system.

Unit dose inhalation devices taught in the art typically involve relatively complicated delivery systems that are relatively heavy, bulky, and costly to manufacture. In addition, most passive dry powder inhalation devices suffer from flow rate dependence issues in which drug delivery may vary from low to high flow rates. Some devices require substantially low pressure to be generated by the patient to operate properly and receive the drug effectively. Generating significant low pressure can be difficult to achieve especially for young and elderly patients. In many cases, the inhalation device technologically taught in the art does not provide adequate feedback features to inform the patient or health care provider if: 1) inhalation device is activated and ready for use, 2) powderized drug is available for inhalation, 3) powderized drug has been delivered, or 4), and inhalation device has been used and is ready to be disposed of.

In US 2012/0132204 (Lucking, et al.), there is described an inhalation device with a simple flow-through powderized drug storage chamber. In this device, air flows through the air gap present after the activation strip is removed from the rear of the inhalation device. Air flows in a non-specific flow pattern to entrain the powderized drug and deliver it straight through the inhalation device and to the patient. The amount of air and resistance of air flow entering the drug storage chamber is susceptible to sink and flatness irregularities in the molded or formed components and compressive forces applied by the patient's hand while operating the inhalation device. Powderized drug is not cleared from the powder storage chamber with a controlled flow pattern leaving the potential for flow dead zones, powder entrapment and drug delivery performance variability especially across a range of flow rates from low to high, 30 L/min to 90 L/min for example. There is no specifically designed means for deaggregating powderized drug besides the flow transition from the powder storage chamber to the fluidly connected channel.

A second embodiment is described with a circulating spherical bead powder dispersion chamber separate and downstream from the powder storage chamber. This embodiment involves more complication with moving beads acting as a mechanical means to grind, and break up powder aggregates as part of the dispersion process. The separate chambers and fluidly connected channel create relatively high surface area for powderized drug including the finer respirable particles to attach and fail to emit from the inhalation device. The circulating beads are driven by air flow generated by the patient, which can vary dramatically, having an effect on performance with such inhalation driven mechanisms. In addition, these types of mechanisms require substantial low pressure to be generated by the patient to actuate.

In U.S. Pat. No. 6,286,507 (Jahnsson, et al.), there is described an inhalation device with a simple powder storage chamber separate from the powder deaggregation means which is located in the fluidly connected channel. Having these two design elements separate creates significant device-drug contact surface area and the potential for substantial drug hold-up due to finer more respirable particles with less mass and momentum attaching to the contact surfaces. In addition, the activation strip is removed from the rear of the device, not providing mouthpiece obstruction and obvious indication to the patient that the device needs to be activated.

SUMMARY

There is a need to have a safer, more efficient, and more cost effective option for delivering inhalation therapies than is currently available. The present invention fulfils that need by providing a dry powder inhalation device for the inhalation of a pre-metered amount of pharmaceutical or nutraceutical dry powders, including single and multiple active ingredient blends and excipients designed to address, but not limited to, the aforementioned unmet needs while providing consistently safe and effective pulmonary drug delivery. Examples of applications for use are, but are not limited to; meeting the needs of infrequent users, delivery of vaccines, drug delivery in institutional settings and drug delivery for bio-defense or any other applications where delivery of a dry powder is necessary or desired.

Some of the advantages of using the disclosed inhalation device over the other alternatives are: drug stability by use of a protective overwrap for each individual dose, easily bar coded or pre-bar coded, intuitive, easy to administer and use, minimal size and weight, efficient dose delivery, low air flow resistance, simple construction, low cost to manufacture, disposable, minimizes human cross contamination such as viral or bacterial, consisting of minimal materials reducing the environmental impact, reliable operation without moving parts and mechanisms, visual dose delivery indicator, visual inhalation device readiness indicator, no coordination required, no cleaning required, no maintenance required, dose advancement is not required, electrical energy source is not required, propellant is not required, capsule handling is not required, dose counter is not required, multi-dose deterrent is not required, mouthpiece cover is not required, it is modular and may be packaged as multiple inhalation devices, may be packaged as multiple inhalers each with different drug formulations, one inhalation device may contain two toroidal chambers with two different drug formulations.

Accordingly, in one embodiment the present invention is a metered dose inhalation device for inhalation of a dry powder by a patient comprising:
a) a body having an exterior and an interior;
b) a toroidal disaggregation chamber in the interior of the body having a bottom portion wherein the dry powder is sealed within at least a portion of the toroidal chamber by a removable partition wherein when the partition is removed the dry powder is delivered to the entire toroidal chamber;
c) at least one air intake passage in fluid communication with the exterior of the body and the interior of the toroidal chamber which directs inlet air toward the bottom of the toroidal chamber at a non-tangential angle when the partition is removed; and
d) an exit passageway in fluid communication with the exterior of the body and the interior of the toroidal chamber when the partition is removed such that upon the inhalation by the patient on the exit passageway, air is drawn from the air intake passage to the toroidal chamber to the exit such that dry powder is carried out the exit passageway to the patient.

Accordingly, in another embodiment of the present invention, there is a metered dose inhalation device for inhalation of a dry powder by a patient comprising a toroidal disaggregation chamber.

DETAILED DESCRIPTION

Figure 1:
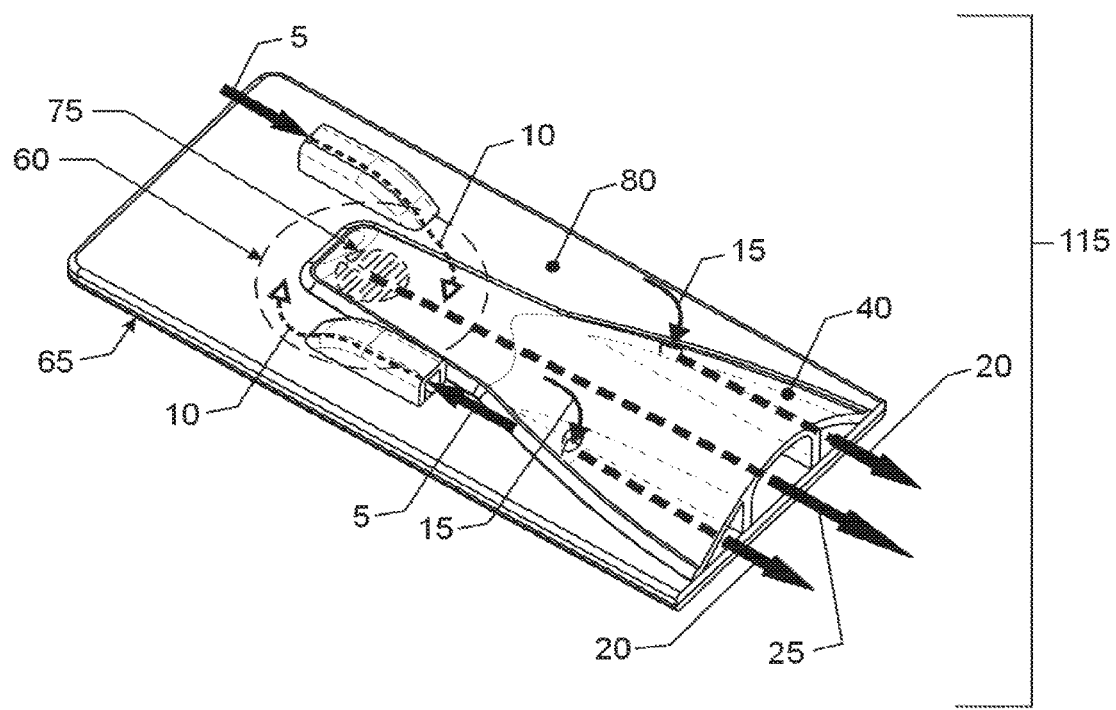
FIG. 1 is an overview of the invention depicting its main elements such as body, channel, air intake passages, air outflow passages, drug flow and toroidal chamber.

While this invention is susceptible to embodiment in many different forms, there is shown in the drawings, and will herein be described in detail, specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

Definitions

The terms "about" and "essentially" mean±10 percent.

The terms "a" or "an," as used herein, are defined as one or as more than one. The term "plurality," as used herein, is defined as two or as more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment," "certain embodiments," and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C." An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used hereinafter, the terms "device," "device of the present invention," "present inhalation device," "inhaler" or "inhalation device" are synonymous.

As used hereinafter, the terms "body," "case" and "housing" are synonymous and refer to the inhalation device as a whole. The body has an exterior and an interior portion.

As used herein the term "inhalation device" refers to a device where a patient inhales on the device to draw a dry powder into the patient. Typically, this is done to draw a medicament into the lungs of the patient, in one embodiment, the device is constructed for a single use.

For the purpose of this disclosure, the term "deaggregation" is synonymous with deagglomeration and disaggregation describing the break-up of like or unlike particles to form a more uniform suspension of the powder in a stream of air.

As used herein a "toroidal disaggregation chamber" refers to a chamber having a toroidal shape. In general, in one embodiment that is a torus shape but any general toroidal shape such as tapered squared or the like will work in the present invention. The chamber is positioned on the interior of the body of the device. Sealed within the chamber, in just a partition of the chamber, is a dry powder. The powder is sealed in place by a removable partition. The partition separates the rest of the chamber from the dry powder such that when the partition is removed the dry powder is exposed to the entire toroidal chamber.

As used herein the "removable partition" or "activation strip" is a device that holds the dry powder within a portion of the device such that when the partition is removed the dry powder can move to the entire interior of the toroidal chamber. In one embodiment the partition has a tab which can be pulled from the exterior of the body to remove the partition. The removable partition or activation strip may be made of the following materials: Peelable aluminum foil structure, foil structure, polymer film or polymer laminate, cellulose, cellulose lamination, wax coated, biodegradable or compostable materials.

As used herein the "air intake passage" refers to an air inlet in fluid communication to the air on the exterior of the device to the interior of the toroidal disaggregation chamber. Air entering the air intake passage is delivered to the toroidal chamber. In an embodiment, the inlet air is aimed at a non-tangential angle for example at an angle toward the bottom of the toroidal chamber. In the present invention there is at least one and in another embodiment there are two, in yet another embodiment, there are two opposing air intake passages. In yet another embodiment the passages are on the same side of the body.

As used herein an "exit passageway" is a passage in fluid communication with the exterior of the body and the interior of the toroidal chamber such that upon the inhalation by the patient on the exit passageway, air is drawn from the air intake passage to the toroidal chamber to the exit such that dry powder is carried out the exit passageway to the patient. In one embodiment, the exit passageway widens as it exits the device body. In another embodiment, it widens sufficiently for a patient to place their mouth on the exit for inhalation of the powder within the toroidal chamber. In one embodiment the exit passageway has air flow channels.

For the purpose of this disclosure, the term "drug" includes both pharmaceutical and nutraceutical compounds including any formulations including excipients. All mentions of drug refer to powderized drug.

For the purpose of this disclosure, the term "powder" is synonymous with powderized drug and includes both pharmaceutical and nutraceutical compounds including any formulations including excipients.

pMDI is a pressurized metered dose inhaler designed to deliver drugs by metering doses from a propellant filled reservoir and aerosolizing doses by release of the propellant energy.

DPI is a dry powder inhaler designed to deliver powderized drugs to the lung either passively using only the patient's inspiratory effort or actively utilizing an external energy source along with the patient's inspiratory effort to disperse and deaggregate powderized drug.

The disposable breath actuated dry powder drug inhalation device has a powderized drug storage chamber integral to a toroidal chamber and air flow pathways for entraining and breaking up powder aggregates prior to inhalation of the powder by the patient. The toroidal chamber is fluidly connected by one or more air inlets directed in a non-tangent manner toward the powder to loft and set up an irregular-rotational flow pattern. Also in fluid connection with the toroidal chamber is a centrally located air and powder outlet consisting of one or more holes forming a grid or hole in fluid connection with a channel providing a passageway for drug flow to the patient. Upon actuation of the inhalation device by breath induced low pressure from the patient, inlet air enters the toroidal chamber causing powder aggregates with greater mass and centrifugal force to circulate toward the outer was for greater time duration than smaller particles. The first stage of impact forces are applied to powder aggregates as they collide with each other and the walls of the toroidal chamber. Additionally, a second stage of forces are applied to powder aggregates as they flow through the intersecting irregular-rotational and non-tangent inlet airstreams subjecting particles to air shear forces, velocity and directional changes. The resulting powder is partially deaggregated and these smaller particles with less mass and centrifugal force flow to the chamber outlet where additional third stage impact forces are applied due to collisions with the outlet grid or hole structure and particle bounce between the toroidal chamber-outlet grid or hole interface ("interface"). In one embodiment, the chamber outlet is centrally located. Deaggregated powderized drug then flows from the outlet grid or hole through the fluidly connected channel to the patient.

Figure 2:
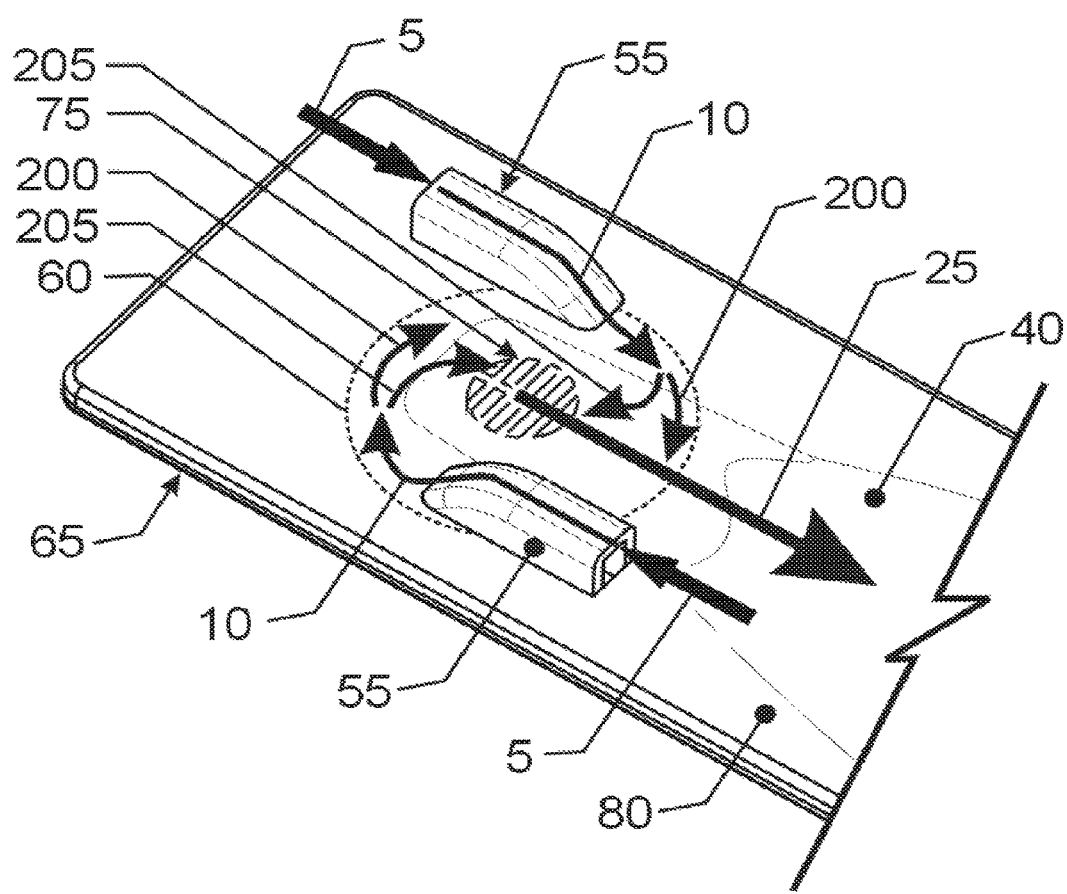
FIG. 2 presents a detailed view of the air intake passages, internal air and drug flow and function of the toroidal chamber.

Now referring to the drawings, FIGS. 1 and 2 depict a perspective view of an embodiment of the present invention with FIG. 2 showing a more detailed perspective view. This embodiment in FIG. 1 is an inhaler with the removable partition removed 115. This is the device in use since, with the partition in place; the device is designed for storage until use. The inhaler 115 consists of a body which, in this embodiment, consists of an upper inhaler body 80 and a lower inhaler body 65. This inhaler has an exterior with the mechanics disposed on the interior of the device. In use, a patient would place their mouth over the area where air exits the inhaler 115. This is indicated by bypass air flow channels 20 and powderized drug and airflow channel 25 both of which deliver to the patient when the patient inhales. Upon inhalation, air enters the air intake passage 5 and travels downward at an angle in a non-tangential manner 10 and into the toroidal chamber 60 which is shown in this figure as a circle, a 3D view will be seen in other figures. This embodiment has two air intake passages 5 which are positioned on the top 80 of inhaler 115. Air swirls in the toroidal chamber 60 and swirls dry powder (not shown in this view) breaking up any agglomerates of powder until air and powder exit through outlet grid 75 to create a fluid communication of the drug and air flow with exit passageway formed by component 40. Aerosolized powder enters an area of exit passageway in 40 wherein there are multiple passage channels. Airflow regulator openings 15 allow air flow resistance tuning by sizing the openings to regulate how much air passes through channels 20 and main channel 25 with delivering the powder exiting from main channel 25. Sizing of the powder exit 75 the holes providing entry of regulator flow 15 determines the air flow resistance level and therefore, the inspiratory effort required to inspirationally actuate the inhaler 115. The preferred embodiment includes a mechanical stop integrated into the inhalation device body providing a stop point for insertion into the patient's mouth thereby providing indication to the patient that the appropriate engagement depth has been achieved to safely and effectively operate the inhalation device by breath actuation.

FIG. 2 shows this airflow/drug flow in a close up perspective view of the inhaler 115. Because bigger aggregated particles will tend to flow around the outer circumference 200 of the toroidal chamber 60, they are subjected to impact forces and break up before flowing to the outlet grid 75. As shown in FIG. 2, the toroidal chamber 60 is designed to utilize the centrifugal force of irregular-rotationally flowing powder aggregates with relatively large mass to partially break-up by impacting each other and the walls of the toroidal chamber yielding finer particles with reduced mass and centrifugal force. Additionally, a second stage of forces are applied to powder aggregates as they flow 200 through the intersecting irregular-rotational and non-tangent inlet airstreams 10 subjecting particles to air shear forces, velocity changes, directional changes, and particle-to-particle collisions. Smaller drug aggregates or particles with reduced mass and centrifugal force may then flow to the toroidal chamber outlet grid or hole interface 75. As particles begin to get smaller due to the forces inside the toroidal chamber 60 they move closer and closer toward the outlet grid 75 near the center of the toroidal chamber 60 till they exit the grid 75 and enter the airflow pathway 25 in the exit passageway of component 40.

Figure 3:
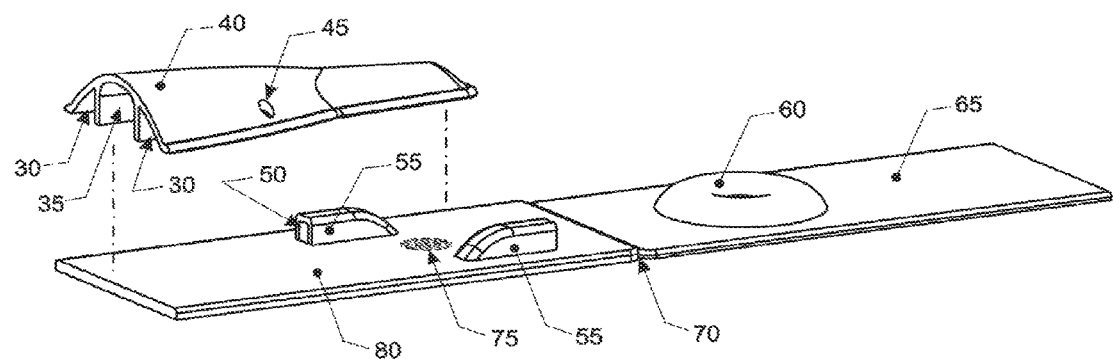
FIG. 3 presents the assembly of the channel component to the inhalation device body with the living hinge in the open state.

FIGS. 3 through 9 depict a perspective view of the construction of an inhaler with the activation strip 95. FIG. 3 depicts the inhaler body molded from a single piece of material the exterior of the body top 80 and exterior bottom 65 are shown in this view. The toroidal shape of the toroidal chamber 60 can clearly be seen in this view. The exit passageway component 40 is mounted on the exterior of upper side 80 creating the bypass channels 30 and drug/air channel 35. The bypass air holes 45 are shown in this view. The upper 80 and lower 65 body are joined by a living hinge 70, a molded strip, such that the upper 80 and lower 65 portions of the body are molded as one piece.

Figure 4:
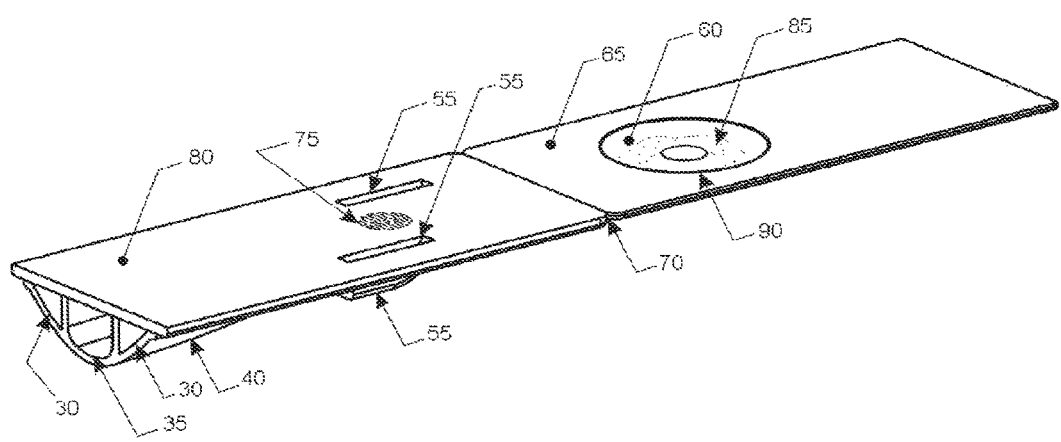
FIG. 4 presents the inhalation device with the living hinge in the open state and drug filled into the toroidal chamber.

FIG. 4 shows the interior surface of upper body 80 and lower body 65. Clear in this view is the interior surface of the toroidal chamber 60 showing powder 85 in the chamber 60. Because the removable partition is not added, the powder merely sits in the bottom of chamber 60. An attachment area 90 for the partition is shown which can include an adhesive material for adhering a partition.

Figure 5:
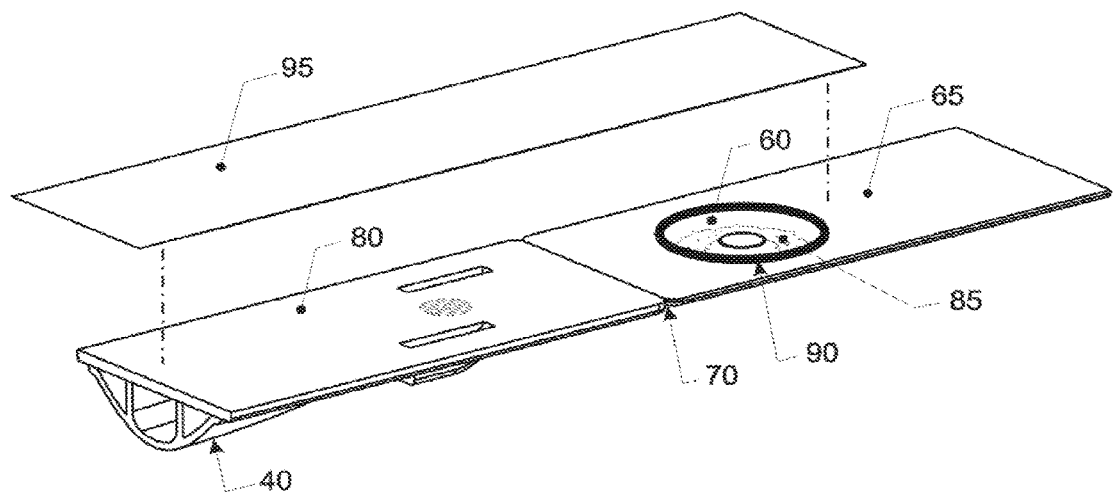
FIG. 5 presents the inhalation device with the living hinge in the open state and drug filled into the toroidal chamber and activation strip positioned over the seal or attachment area around the toroidal chamber.
Figure 6:
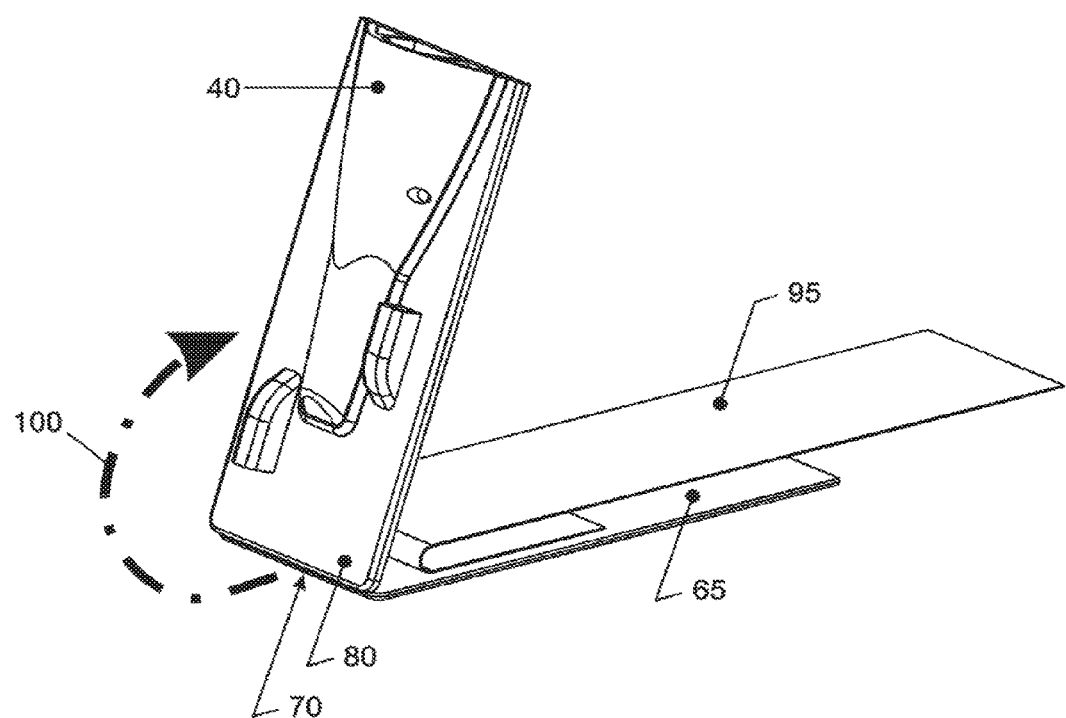
FIG. 6 presents the inhalation device body being closed and the attached activation strip being folded with the drug contained within the toroidal chamber.
Figure 7:
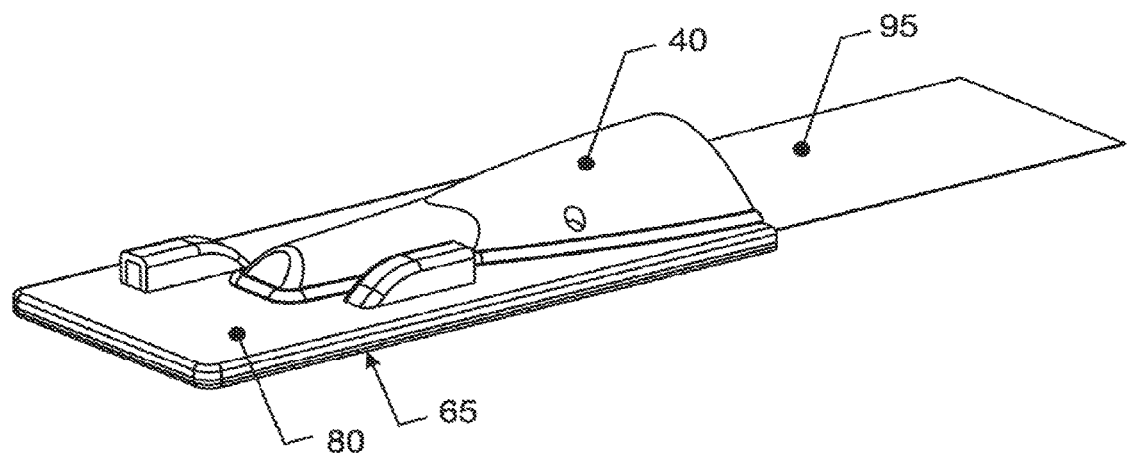
FIG. 7 presents the inhalation device with drug contained within the toroidal chamber, activation strip sealed and folded and perimeter of the device body sealed or joined.
Figure 8:
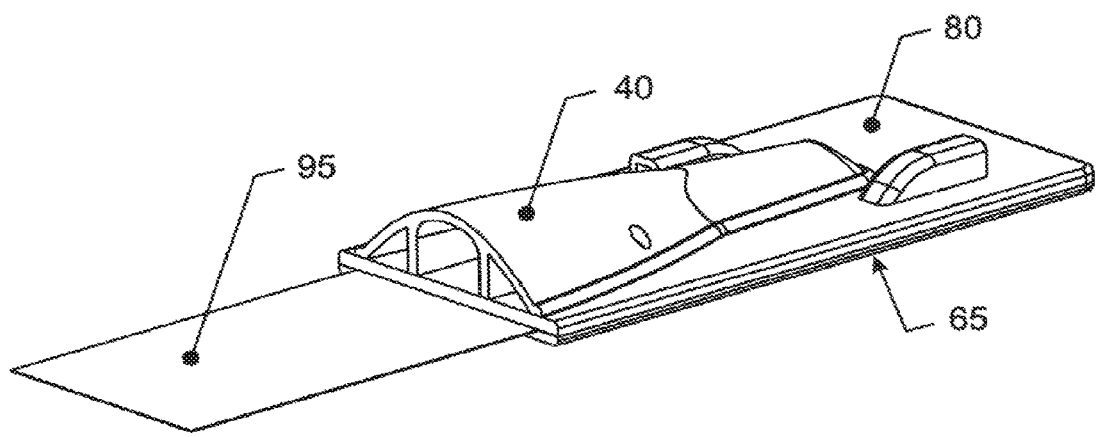
FIG. 8 presents a different perspective view of FIG. 7.
Figure 9:
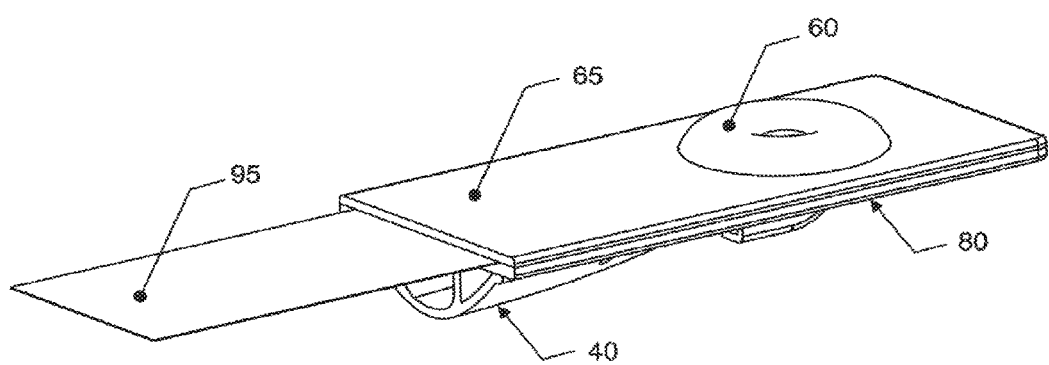
FIG. 9 presents a different perspective view of FIG. 7.
Figure 10:
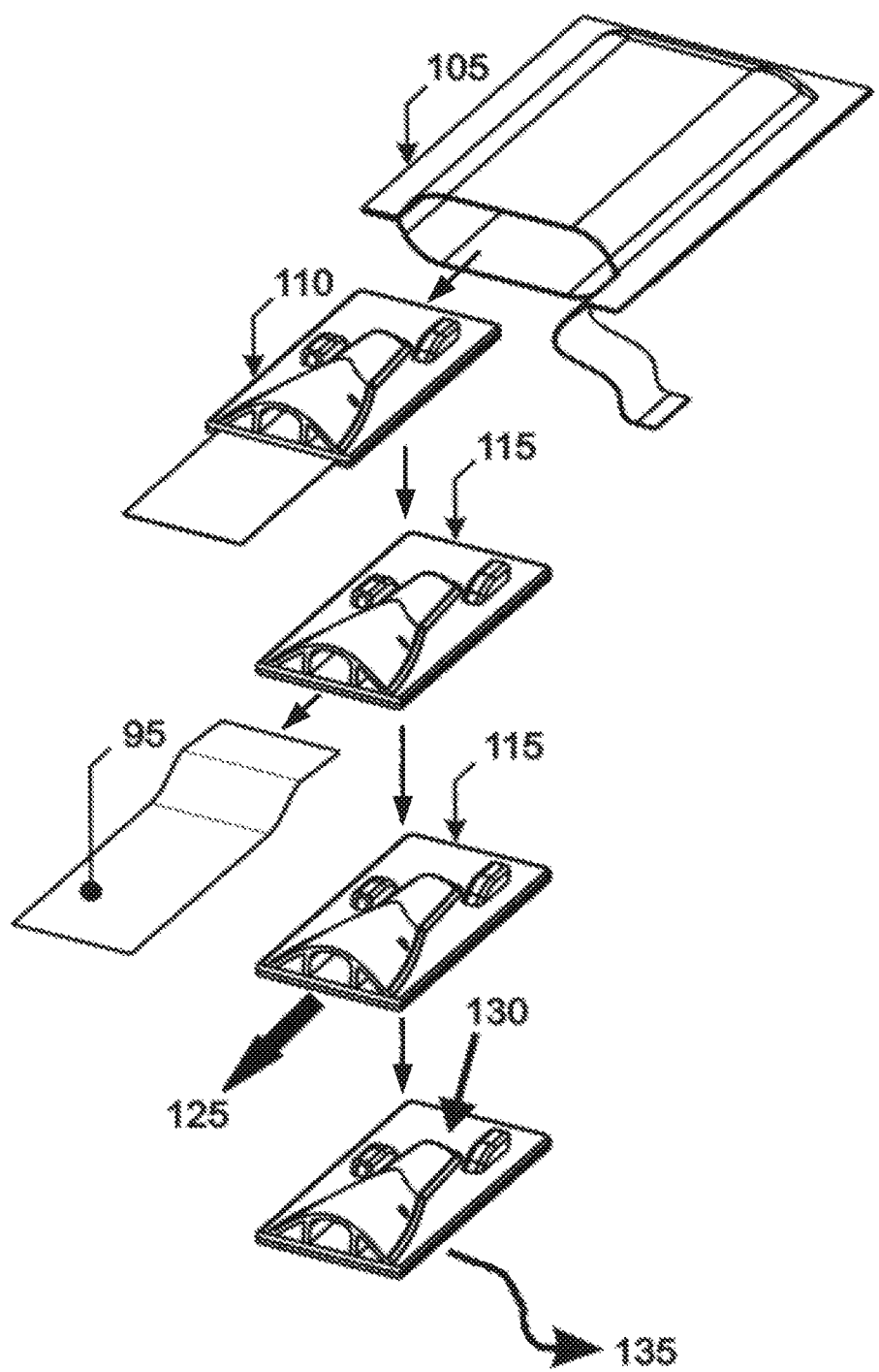
FIG. 10 is an illustration of use of the inhalation device including protective overwrap.
Figure 11:
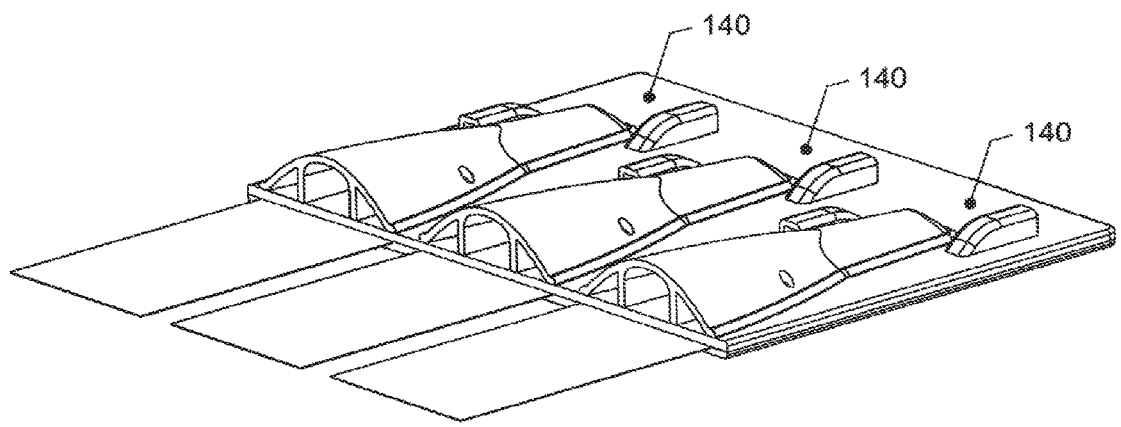
FIG. 11 presents an example of a multi-dose embodiment with multiple doses of the same drug available for inhalation.
Figure 12:
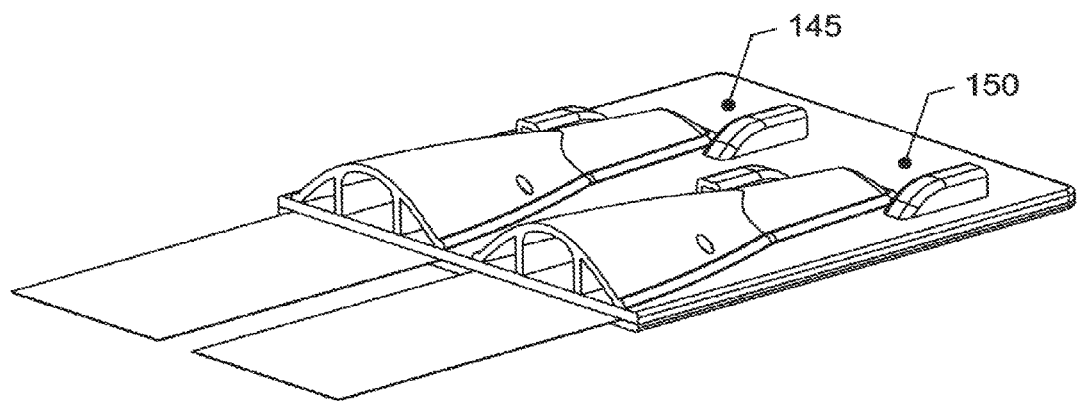
FIG. 12 presents an example of a multi-dose embodiment with different drugs available for inhalation.
Figure 13E:
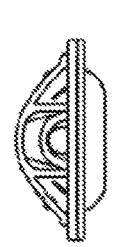
FIGS. 13A-13E present a top view, a side view, a bottom view, a rear view, and a front view, respectively.
Figure 13A:
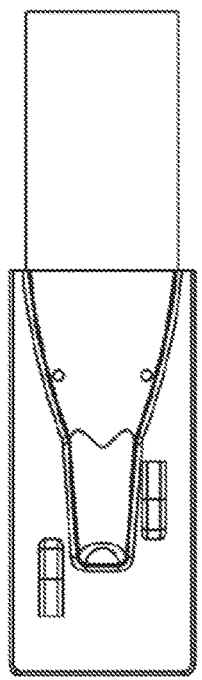
Figure 13B:
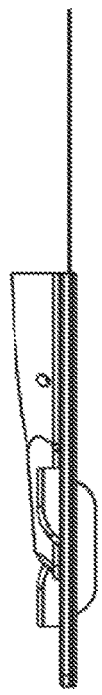
Figure 13C:
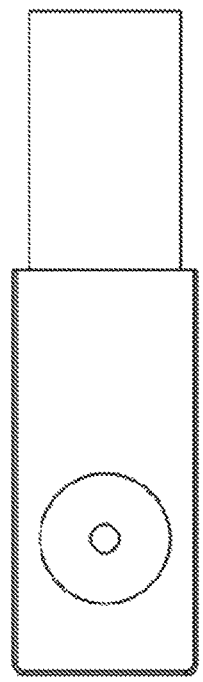
Figure 13D:

In FIG. 5 a partition 95 is placed on the interior surface of body portions 80 and 5 covering entirely toroidal chamber 60 from delivering powder to the flow pathway of the inhaler. FIG. 6 shows the folding 100 of the upper body 80 to meet the lower body 65 folding the removable partition. In FIG. 7 an embodiment of the present invention inhaler is completely constructed and noted as inhaler 110 in the following figures.

FIG. 8 depicts a perspective view of the same inhaler 110 as shown in FIG. 7 however, from a different view which allows a view of the exit passageway of the inhaler 110. FIG. 9 shows a bottom perspective view of inhaler 110.

FIG. 10 is a perspective series of views of opening, removal of the partition and use of inhaler 110 in a single use embodiment. An embodiment of the present inhalation device 110 as shown in FIG. 10 is protected from contamination, ultraviolet light, oxygen, if required, and water vapor ingress by a surrounding protective overwrap 105 such as, but not limited to, aluminum foil laminates joined to contain the inhalation device as individually packaged or joined in a strip, sheet, or roil form with individually removable inhalation devices by shearing or pulling apart for as-needed access to inhalation devices from a multi-dose package. In addition, either of the aforementioned protective overwrap packaging configurations providing printable area for color coding and bar coding for scanning into electronic charting systems and providing general information to patients and administrators.

As shown in FIG. 10, the preferred embodiment requires, but is not limited to, a minimal number of steps as disclosed below to administer or self-administer the dry powderized drug.

Open the protective overwrap 105 packaging

Pull the activation strip by the end and remove it

Have the Patient Inhale 125 the powderized drug

Dispose 135 of the inhalation device and protective overwrap

This embodiment of the inhalation device may be disposed of after use to help facilitate clean environments of use or administration by reducing the chance of person to device to person transmission of hazardous matter such as viruses and bacteria.

As shown in FIG. 10, patient feedback inhalation device status indicators include the obstruction of the mouthpiece by the activation strip because of its length in the assembled state 110, providing indication to the patient that activation strip 95 removal is required prior to inhaling 125 the powderized drug. The indicators also include the use of transparent materials for the inhalation device body or powder storage chamber providing visibility of the drug before and after use for confirmation of drug delivery by visual inspection 130. In FIG. 10, 105 depicts the protective overwrap, 110 shows the device removed from the protective overwrap, 115 depicts the inhalation device with the activation strip 95 removed and drug ready for inhalation, 125 arrow illustrates breath actuation by the patient 125 and 135 represents disposal of the used inhalation device.

An additional embodiment is a multi-dose strip as shown in FIG. 11 comprised of inhalation devices integrated and packaged as one with each toroidal chamber containing the same powderized drug formulation 140 drug "A."

An additional embodiment is a multi-dose strip as shown in FIG. 12 comprised of inhalation devices integrated and packaged as one. One side of the inhalation device may contain powderized drug "B" 145 and the other side powderized drug "C" 150 as well as additional drugs.

An additional embodiment includes multiple inhalation toroidal chambers fluidly joined to one powder exit passageway and patient interface mouthpiece. Each toroidal chamber may contain different powderized drugs.

FIGS. 13A-13E depict a series of orthogonal views of inhaler 110.

FIGS. 14A and 14B depict a series of views of embodiments including an activation strip 95 designed to retain and protect the powderized drug in the toroidal chamber by closing off a region of the chamber (and in some embodiments the entire chamber). Removal of the activation strip 95 "activates" the inhalation device exposing and fluidly connecting powderized drug 85 residing in the toroidal chamber 60 to one or more inlet airways 55 and outlet grid or hole 75. This prepares the inhalation device 115 for dose delivery to the patient when low pressure breath actuation (inhalation) occurs. The activation strip 95 may be removable from the inhalation device and disposed of separately. The aforementioned design is useful due to its simplicity and intuitiveness for the user. An alternate embodiment may include a shifting activation strip. In this embodiment, shifting or moving the activation strip from one position to another activates the inhalation device 115 while remaining retained within the inhalation device 115. The activation strip may be assembled or joined, but not limited, to the following methods; heat sealing, captured in place mechanically, adhesive, peelable adhesive, friction fit, press fit, snap fit, laser welded, radio frequency or ultrasonic welding. It may be assembled or joined to the inhalation device with or without folds. Folding 100 the activation strip 95 along with the inhaler body during assembly as shown in FIG. 6 results in a peelable attachment to facilitate activation by shearing the peelable bond area 90 FIG. 5 between the activation strip and inhalation device body. The activation strip 95 may provide printable area for color coding and bar coding for scanning into electronic charting systems and providing general information to patients and administrators.

As shown in FIGS. 14A and 14B, the embodiment includes an integrated toroidal powderized drug storage and deaggregation chamber 60 designed to retain and protect the powder 85 during storage and provide the means to deaggregate the powder during the breath actuation event. The toroidal chamber 60 design is an improvement over the prior art due to its reduced powder-inhalation device contact surface area, reducing powder hold-up (losses) in the device, controlled and efficient air and drug path and simplified construction. Integration of the powder storage chamber and deaggregation chamber into one simplifies inhalation device design and reduces powder to inhalation device contact surface area resulting in reduced powder losses and therefore improved drug delivery performance. The toroidal chamber consists of an outside wall 265, inside wall 260, outlet grid or hole 75 interface region which is the air gap between 75 and 155 bottom and top surfaces.

In FIGS. 14A and 14B the toroidal chamber geometry includes a raised central axis located region 270 that guides drug particle flow to the chamber outlet grid or hole 75 eliminating an air flow dead zone at the bottom of the chamber where powder 85 would normally collect and fail to be delivered to the patient. The flow pattern within the toroidal chamber 60 is irregular and not a truly circular path due to the intersecting non-tangent inlet air streams 10 disrupting circular flow and modifying the flow path into an irregular-rotational path.

Figure 14A:
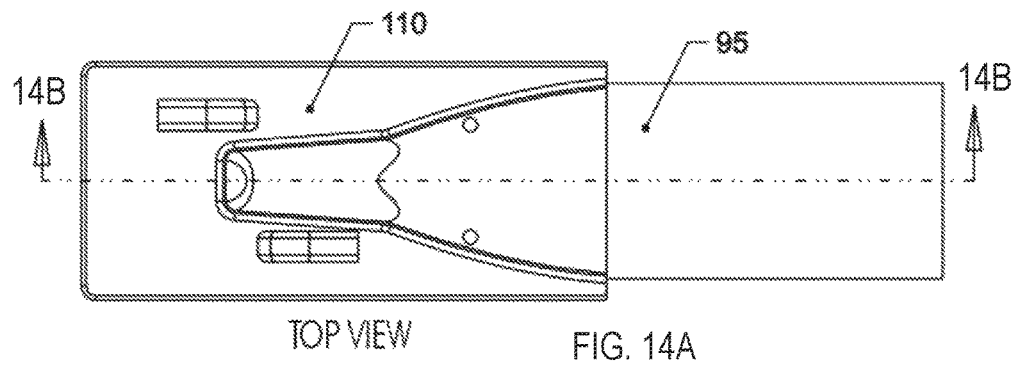
FIGS. 14A and 14B present a top view and a cross-sectional view.
Figure 14B:
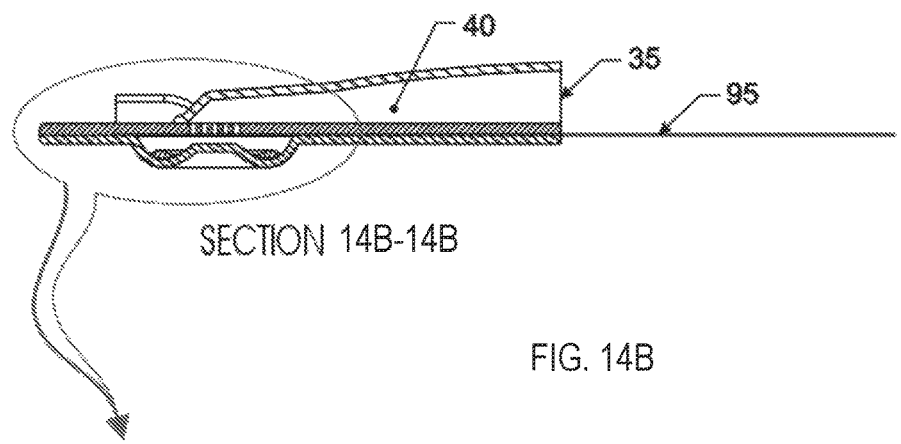
Figure 14C:
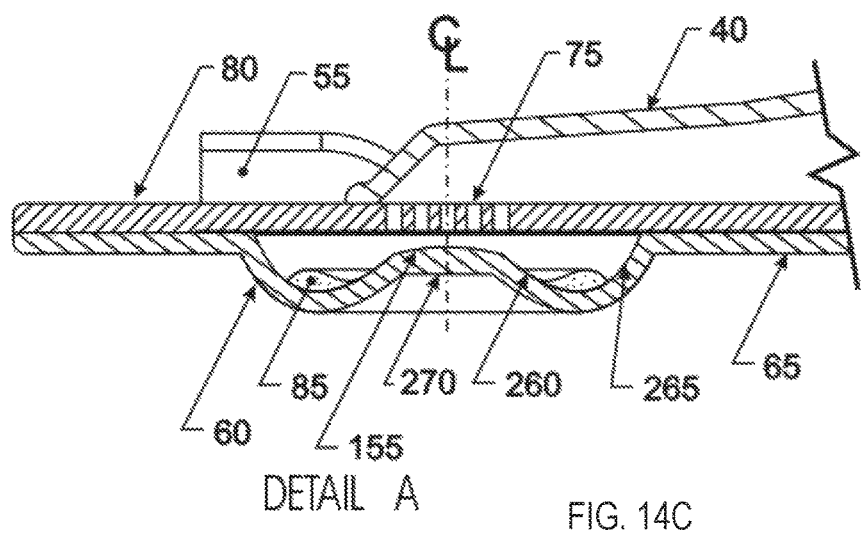
FIG. 14C presents a detailed cross section of the toroidal chamber illustrating key features.

The following is applicable to both toroidal and full torus chambers; for the purpose of illustration in this disclosure, the toroidal chamber including inner (example 260, FIG. 14C) and outer surfaces (e.g. 265, FIG. 14C) is shown as various circular toroidal geometries however embodiments are not limited to circular. Additional geometries may be used such as polygonal, polygonal with radiused corners, oval, elliptical or irregular or any combination thereof applied to inner and outer surfaces of the toroidal chamber.

Figure 15A:
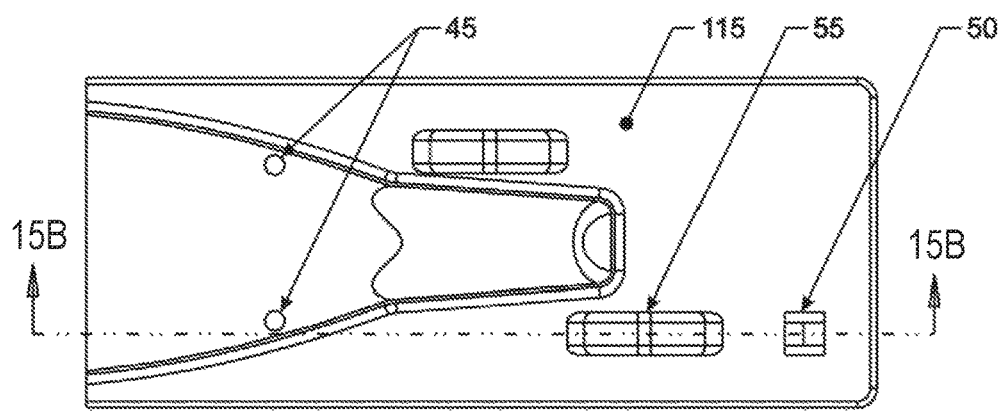
FIG. 15A is a top view and FIG. 15B is a cross section side view illustrating a serpentine inlet, drug spillage, inlet air flow and bypass and outlet air flow.
Figure 15B:
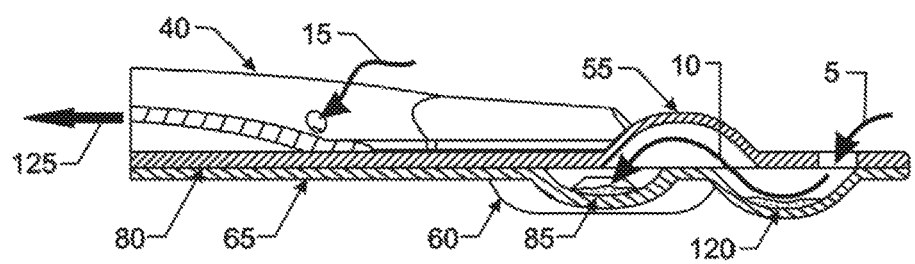

Inlet air 10 may be guided through channel(s) 55, 120 as shown in FIGS. 15A and 15B with redirected pathway(s) creating a holding area(s) 120 for powder in the event, after activation the inhalation device is tilted to the extent drug powder 85 spills into any of the air inlets prior to breath actuation of the inhalation device. The redirected pathway(s) as shown in FIGS. 15A and 15B prevent powder loss when the inhalation device is tilted and retains powder in the holding area(s) 120 for entrainment and flow to the patient during the breath actuation.

Figure 16A:
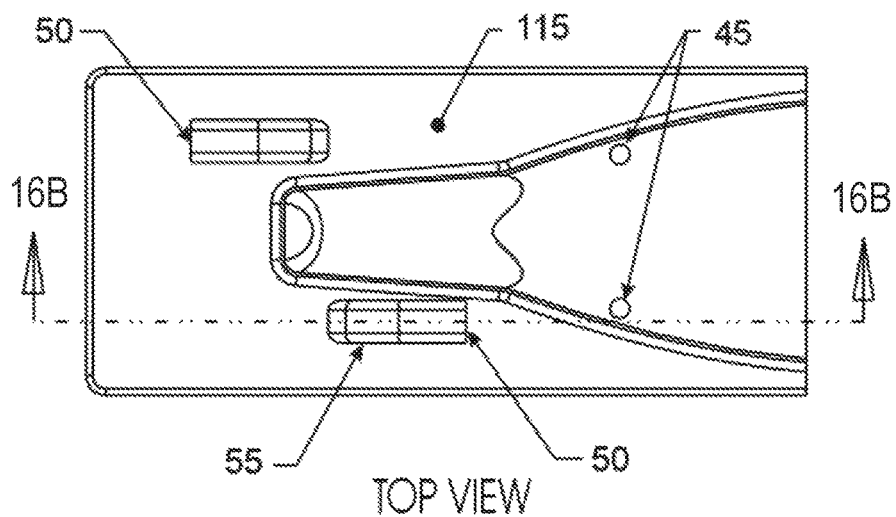
FIG. 16A is a top view and FIG. 16B is a cross section side view illustrating an air inlet, inlet air flow and bypass and outlet air flow.
Figure 16B:
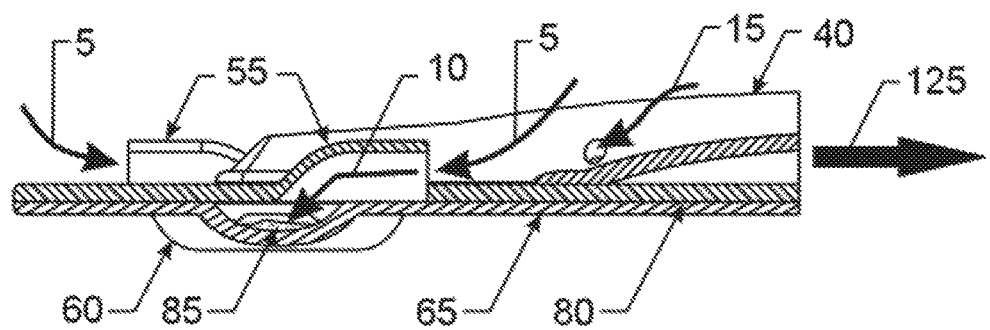

In FIGS. 16A and 16B, upon inhalation, inlet air 10 rushes into the toroidal chamber 60 lofting and flowing the powderized drug 85. The non-tangent inlet air flow paths 10 intersecting the fluidly connected toroidal chamber 60 creates relatively high air flow velocity regions, redirecting the circulating powderized drug 85 into an irregular-rotational flow pattern. This intersection of the air flow paths provide air shear forces, velocity and directional changes to flowing particles further deaggregating the powderized drug 85. Inlet air may be guided through channels 55 with the geometry designed to direct flow non-tangentially toward the powder or elsewhere to achieve the desired drug delivery performance.

Figure 17:
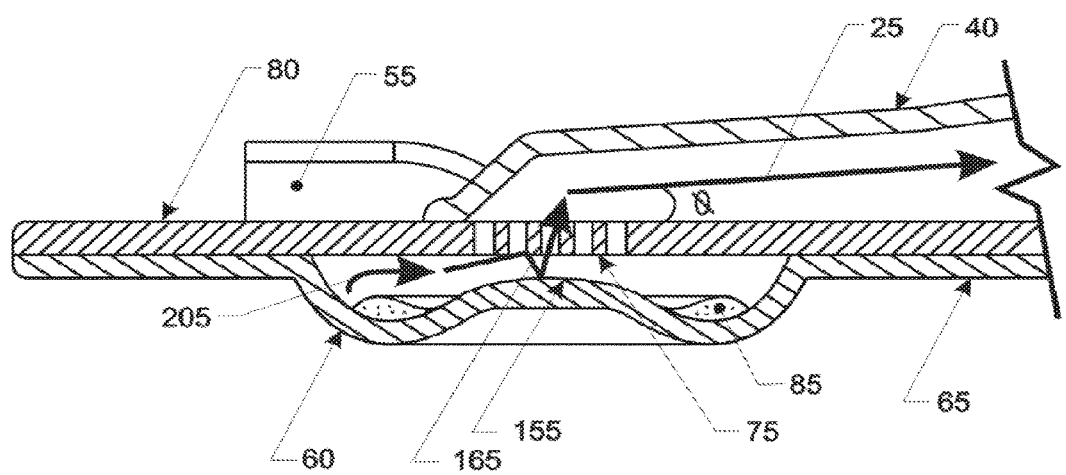
FIG. 17 illustrates drug flow from the toroidal chamber, through the outlet grid-toroidal chamber interface and through the channel for exit to the patient.
Figure 18:
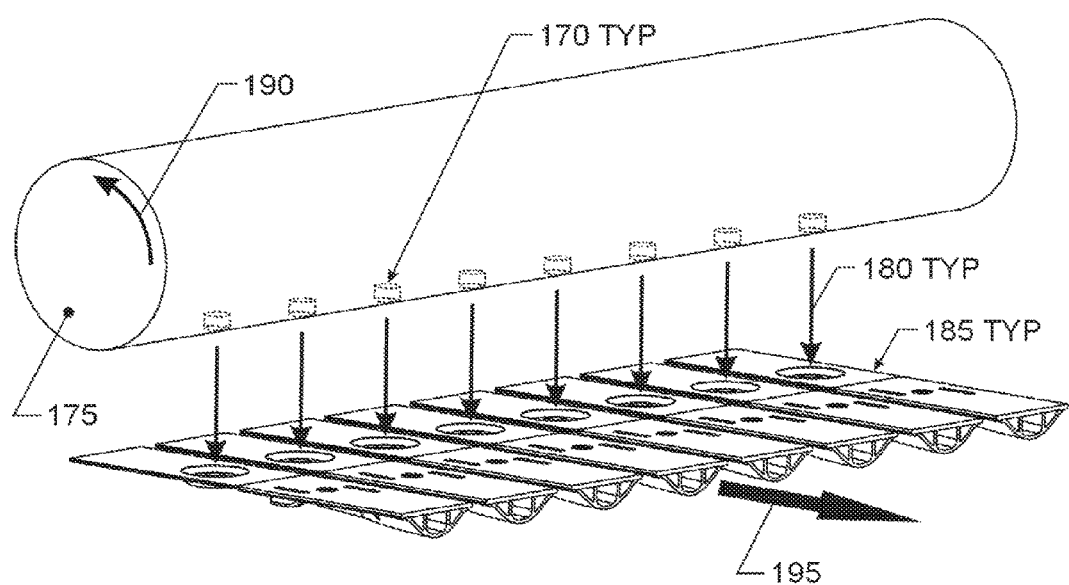
FIG. 18 presents drug powder filling into inhalation devices by use of a common 'drum' filling system.
Figure 19:
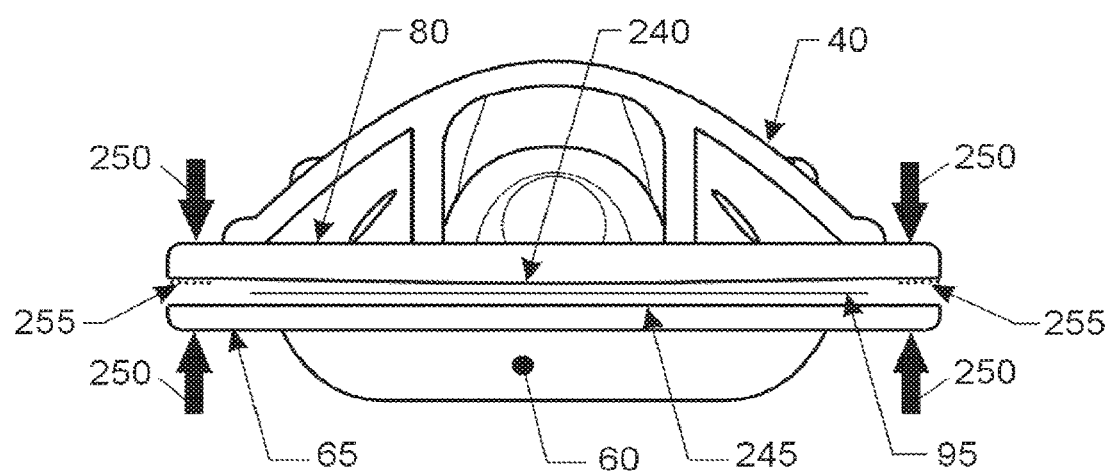
FIG. 19 presents a front view of the inhalation device with one rigid body member and one conformable, forced and attached during assembly to reduce the air gap between the two body members.
Figure 20:
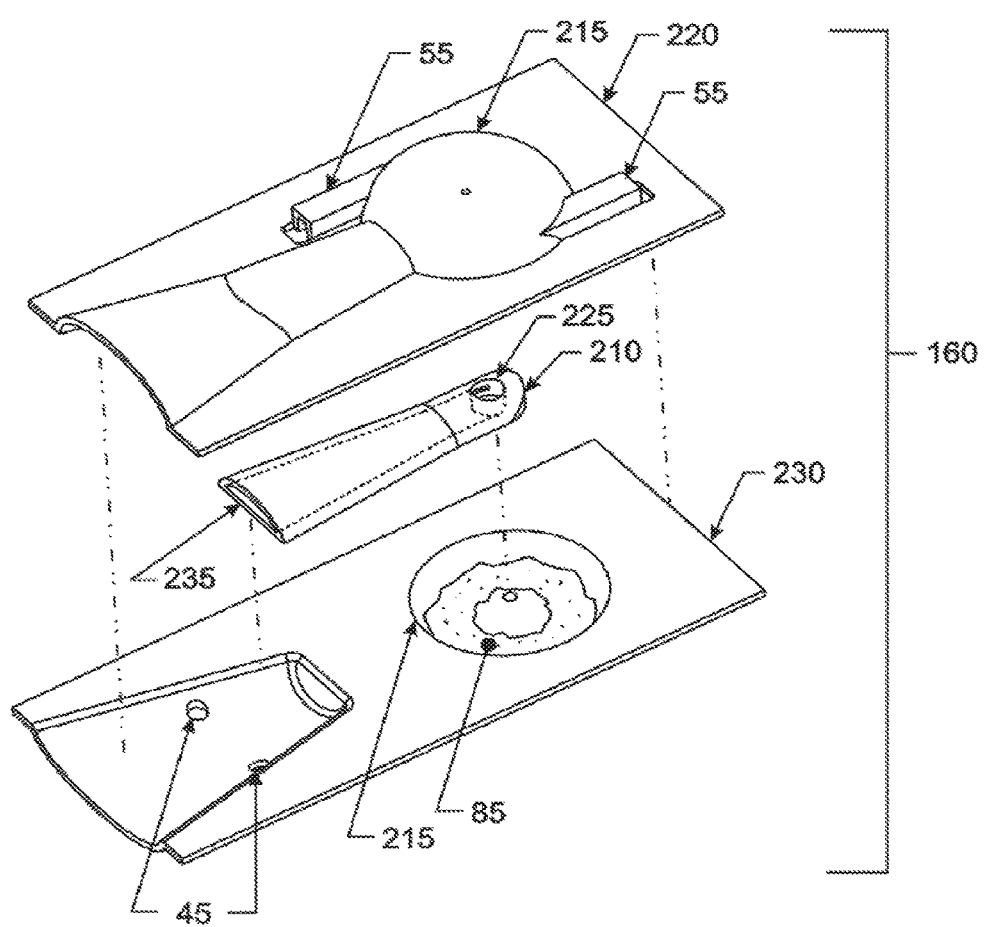
FIG. 20 presents an alternate full toroidal chamber embodiment.
Figure 21A:
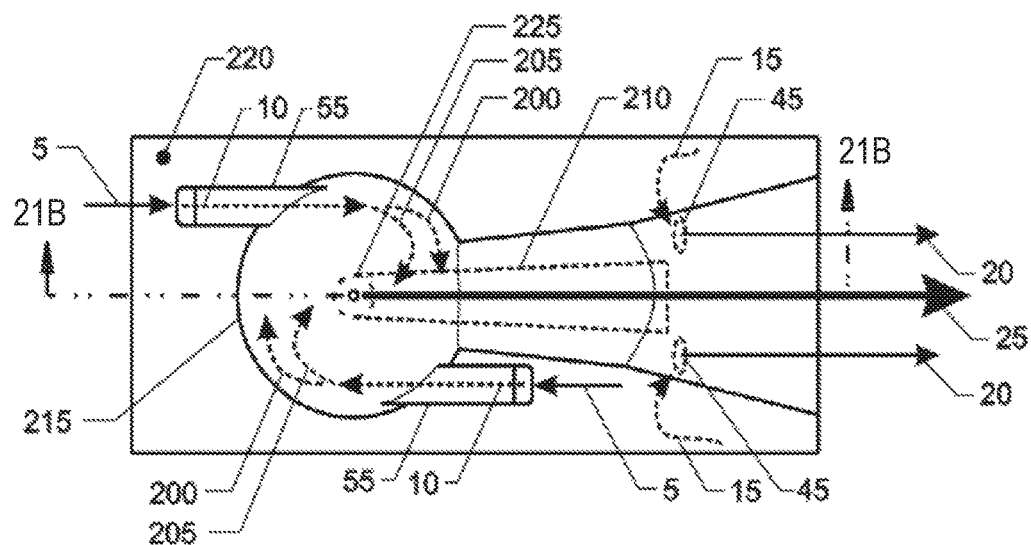
FIGS. 21A-21C present orthogonal and sectional views of an alternate full toroidal chamber embodiment.
Figure 21B:
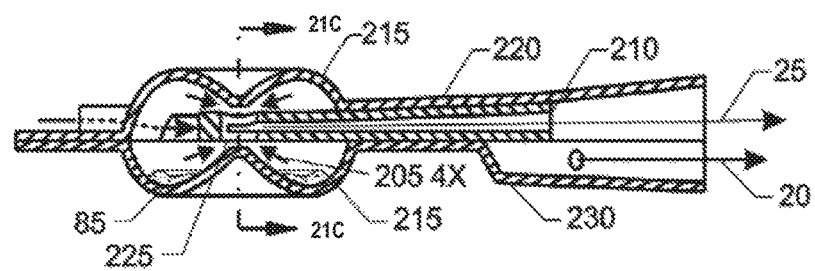
Figure 21C:
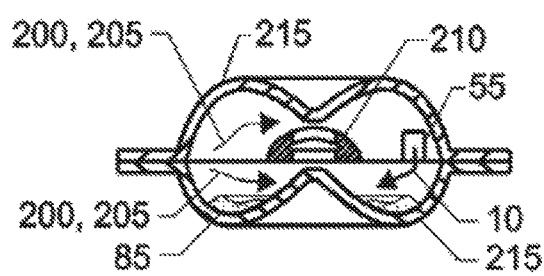

FIG. 17 depicts where the powder is subjected to additional third stage impact forces as the drug aggregates 205 impacts the rigid surfaces in this air gap region and bounce between the interface surfaces.

In FIG. 17 the embodiment includes an outlet grid or hole 75 fluidly intersecting the toroidal chamber 60 near its center axis providing an opening or openings for flowing powderized drug 205, 165 to exit the toroidal chamber 60 and flow through the fluidly connected channel 35 to the patient. The outlet grid 75 may consist of round holes or any of the following polygonal, radiused polygonal, oval, elliptical, ribbed, stepped, convex, concave, tapered holes, vents, staggered layout, linear layout, radial layout, radial openings, a mesh, a screen, irregular and any combination or reasonable variants thereof. The outlet grid 75 may be substituted with a single hole 75 sized and located to facilitate outlet flow of drug powders with flow properties, particle size and cohesiveness for optimizing drug delivery performance. The single outlet hole 75 may be round, polygonal, radiused polygonal, ribbed, stepped, convex, concave, oval, elliptical, tapered, irregular and any reasonable variant thereof. The outlet flow area is the air and powder flow throttle point of the drug flow passageway in the inhalation device. A design feature is the adjustment of the outlet flow area that determines the air volume, air flow velocity, drug powder impact forces and duration of air flow through the toroidal chamber 60. The outlet flow area is equal to the sum of the area of all holes in the grid or the singular hole area. As shown in FIG. 17, the outlet grid structure 75 including solid partitions or ribbing between and around the outlet grid openings, impart impact forces on the powderized drug as rotationally flowing powder aggregates 205, 165 are forced through the stationary grid. Additionally, the singular outlet hole 75 transition imparts impact forces on the powderized drug as rotationally flowing drug aggregates 205 impact the top surface of the chamber prior to exiting to the fluidly connected channel.

As shown in FIG. 17, an embodiment includes an outlet grid or hole-toroidal chamber interface air gap region formed between surfaces 75, 155 and consisting of an outlet grid or hole 75 and a raised toroidal chamber section 270 with internal surface 155. The air gap formed by this interface defines a region where powderized drug is forced to flow through path 165 during the breath actuation event due to the low pressure differential generated by the patient. Flowing drug particles 165 trying to exit are of various particle size with differing degrees of aggregation. The smaller partides are able to redirect and flow through the outlet opening(s) of 75 while the larger particles with greater mass and momentum impact the solid grid structure of 75 and the surface around the opening. This impact imparts forces on the aggregated drug particles to break them up into smaller more respirable drug particles. The impacting particles are free to bounce back and forth (path 165) in the air gap region between the outlet grid or hole 75 and the raised section of the toroidal chamber 155. The particle bounce effect (path 165) applies additional impacts to the aggregated particles prior to exiting to the fluidly connected channel 35 and flowing to the patient. The geometry of the outlet grid or hole-toroidal chamber interface 75, 155 may consist of many variants. The embodiments are not limited to specific interface geometries but some examples include: point, dome, hemispherical, flat, cone, convex, concave, cylindrical, irregular, conic, stepped and irregular shapes including any combination thereof.

In FIG. 18, the living hinge 70 location on the front or rear surfaces of the inhalation device creates a narrow profile while in the open state for efficiently filling powderized drug into multiple inhalation devices at one time. Each rotation 190 of a powder filling system's "drum" 175 with multiple dosing bores 170 may fill a greater number of inhalation devices 185 per cycle as compared to inhalation devices with a living hinge on a side surface. Due to the living hinge feature 70, additional manufacturing efficiencies may be achieved such as reduced; tooling, handling, automation equipment and supply chain management. FIG. 18, 180 depicts drug powder filling into the empty inhalation devices in the first state 185 and 195 depicts linear indexing of inhalation devices 185 between filling cycles. An alternate embodiment may be constructed without the living hinge 70 as disclosed above. The inhalation device may be comprised of components produced and assembled as individual body components; the separate upper body component 80 and separate lower body component 65.

As shown in FIG. 19, this embodiment includes a means for ensuring air gap closure or minimization between the inhalation device body halves by producing one side convex 240 and the opposite side 245 flat or of a different convex or concave radius. During assembly, the two body halves are forced 250 together and joined along the perimeter area 255 conforming the two body halves 65 and 80 to each other to reduce the air gap(s) in between due to component dimensional irregularities such as sink and warp. The built-in force biasing the two inhalation device body halves 65 and 80 to each other in the assembled state also acts to retain the activation strip 95 and close the activation strip gap after activation thereby preventing air leakage and powder loss in the gap.

As shown in FIGS. 20 and 21A-21C, an alternate embodiment 160 may include an integrated full torus powderized drug storage and deaggregation chamber 215 designed to retain and protect the powder 85 during storage and provide the means to deaggregate the powder prior to delivery to the patient. Integration of the powder storage chamber and deaggregation chamber into one simplifies inhalation device design and reduces drug powder to inhalation device contact surface area resulting in reduced drug powder losses and therefore improved drug delivery performance. The full toroidal chamber consists of a full toroidal shape with outside wall, inside wall, outlet grid or hole 225 interface region, bottom surface, top surface and intersecting channel. The full toroidal chamber 215 is designed to utilize the centrifugal force of irregular-rotationally flowing powder aggregates 200 with relatively large mass to partially break-up by impacting each other and the walls of the full toroidal chamber yielding finer particles 205 with reduced mass and centrifugal force. Additionally, a second stage of forces are applied to powder aggregates 200 as they flow in a rotational path and impact the protruding channel 210 subjecting particles to impact forces, velocity changes and directional changes. Smaller powder aggregates with reduced mass 205 and centrifugal force may then flow to the toroidal chamber outlet grid or hole interface 225 where they are subjected to additional third stage impact forces as the aggregates impact rigid surfaces in this interface 225 region and bounce between the interface surfaces. In addition, the full torus chamber geometry 215 includes raised central axis or near central axis located regions that guide particle flow to the chamber outlet grid or hole 225 eliminating the air flow dead zones at the top and bottom of the chamber where drug powder 85 would normally collect and fail to be delivered to the patient. The flow pattern within the full torus chamber 215 is irregular and not a circular path due to the intersecting channel disrupting circular flow and modifying the flow path into an irregular path. One or more air inlets 55 may be used fluidly connected and intersecting the full toroidal chamber 215 either tangentially or non-tangentially. In FIGS. 20 and 21A-21C, 220 and 230 are inhalation device body components and 235 is the channel outlet fluidly connected through channel component 210 to the outlet hole or grid 225.

The inhalation device may be made from the following materials for example including injection molded polymers, anti-static polymers, thermoformed or pressure formed polymers, cellulose (paper) or partial cellulose laminated material, wax coated laminates, biodegradable, compostable, elastomers, silicone, aluminum foils including laminations, metallic hot or cold formed, glass, ceramic and composite materials or any combination thereof.

The inhalation device components may be produced by the following manufacturing methods: injection molding, thermoforming, pressure forming, blow molding, cold forming, die cutting, stamping, extruding, machining, drawing, casting, laminating, glass blowing.

The inhalation device components may be joined by the following methods: heat sealing, heat staking, ultrasonic welding, radio frequency welding, snap fits, friction fits, press fits, adhesive, heat activated adhesive and laser welding or any combination thereof.

The outlet grid or hole region may be made from the following materials: polymers, anti-static polymers, metal, metal mesh or screen, elastomers, silicone, cellulose, glass, ceramic, wax coated laminations, aluminum including foils and foil laminations, biodegradable and compostable or any combination thereof.

The embodiments reside as wen alone or in sub-combinations of the objects, aspects, elements, features, advantages, indicators, methods and steps shown and described.

It is an object of all embodiments to provide an improved disposable dry powder inhalation device for pulmonary inhalation of pharmaceutical or nutraceutical dry powders including excipients.

The embodiment or embodiments including any sub-combinations of the objects, aspects, elements, features, advantages, indicators, methods and steps may be used in any type of patient in any setting for any therapy in any orientation.

The embodiment or embodiments including any sub-combinations of the objects, aspects, elements, features, advantages, indicators, methods and steps may be used in a multi-dose inhalation device with a separate index-able drug strip or cartridge or replaceable drug blister or capsule.

The embodiment or embodiments including any sub-combinations of the objects, aspects, elements, features, advantages, indicators, methods and steps may be used in a nasal drug delivery device.

The embodiments including any sub-combinations of the objects, aspects, elements, features, indicators, advantages, and methods describe the inhalation device and method for pulmonary inhalation of pharmaceutical or nutraceutical dry powders including excipients.

The embodiments are not limited to the specifics mentioned as many other objects, aspects, elements, features, advantages, methods and steps and combinations may be used. The embodiments are only limited only by the claims. Additional information describing the embodiments are stated in other sections of this disclosure.

It should be understood that the embodiments also reside in sub-combinations of the objects, aspects, components, features, indicators, methods, materials and steps described.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fan within the scope of the invention as claimed by the applicant.

The invention claimed is:

1. An apparatus, comprising:

a body having an upper portion and a lower portion, the body defining a disaggregation chamber, a bottom portion of the disaggregation chamber being within the lower portion and containing a dry powder drug, the lower portion including a raised section extending from an inner surface of the disaggregation chamber, the raised section configured to guide a flow of the dry powder drug within the disaggregation chamber;

a removable partition disposed between the upper portion and the lower portion, the partition retaining the dry powder drug within the bottom portion of the disaggregation chamber when the upper portion and lower portion are coupled together;

an air intake passage configured to place an external volume in fluid communication with the disaggregation chamber when the partition is removed; and an exit passageway configured to place the external volume in fluid communication with the disaggregation chamber when the partition is removed such that upon inhalation by a patient on the exit passageway, air is drawn from the air intake passage to the disaggregation chamber and on to the exit passageway to disaggregate the dry powder drug within the disaggregation chamber and convey the dry powder drug via the exit passageway to the patient.

2. The apparatus of claim 1, wherein a tab portion of the partition extends outside of the body and obstructs a mouthpiece when the partition is disposed between the upper portion and the lower portion.

3. The apparatus of claim 2, wherein:
the mouthpiece is at a first end portion of the body;
an intake opening into the air intake passage is at a second end portion of the body, the second end portion opposite the first end portion; and
the tab portion extends from the first end portion of the body to obstruct the mouthpiece.

4. The apparatus of claim 3, wherein the second end portion of the body includes a hinge that joins the upper portion of the body to the lower portion of the body.

5. The apparatus of claim 3, wherein the partition includes a folded portion between the upper portion of body and the lower portion of the body.

6. The apparatus of claim 3, wherein a flow structure defines a plurality of channels within the exit passageway.

7. The apparatus of claim 3, wherein the exit passageway defines an air bypass channel through which a bypass air flows upon the inhalation by the patient, the air bypass channel separated from a drug delivery channel by a side wall.

8. The apparatus of claim 3, wherein the raised section extends from a central axis of the disaggregation chamber.

9. The apparatus of claim 1, wherein:
the air intake passage is a first air intake passage; and
the upper portion includes a second air intake passage, the first air intake passage producing an opposing flow of air to an air flow within the second air intake passage.

10. A method of using an inhalation device to deliver a single dose of a pre-metered dry powder drug, comprising:
removing the inhalation device from within a protective overwrap packaging, the inhalation device including a body having an upper portion and a lower portion, the lower portion of the body defining a chamber, the body defining an intake channel and an exit channel, the exit channel fluidically coupled to the chamber via an exit opening at a first end portion of the body, the intake channel fluidically coupled to the chamber via an intake opening at a second end portion of the body;
removing a partition of the inhalation device by pulling an end of the partition, the partition disposed between the upper portion of the inhalation device and the lower portion of the inhalation device to retain the dry powder drug within the chamber before the removing, the end of the partition extending beyond the first end portion of the body of the inhalation device and obstructing a mouthpiece before the removing;
placing, after the removing the partition, a portion of the mouthpiece where air exits the exit channel in a mouth of a patient; and
inhaling on the mouthpiece such that intake air is drawn through the intake channel to produce a flow of intake air within the chamber to disaggregate the dry powder drug, the disaggregated dry powder drug exiting the inhalation device via the exit channel.

11. The method of claim 10, wherein the partition includes a folded portion between the upper portion of body and the lower portion of the body.

12. The method of claim 11, wherein the removing the partition includes peeling a bond between the folded portion of the partition and the lower portion of the body.

13. The method of claim 10, wherein the removing the partition includes pulling the end of the partition in a direction from the second end portion of the body toward the first end portion of the body.

14. The method of claim 10, wherein:
the lower portion of the body includes an outer wall defining the chamber; and
the inhaling produces a rotation of the dry powder drug that impacts the outer wall to disaggregate the dry powder drug.

15. The method of claim 10, further comprising:
disposing, after the inhaling on the mouthpiece, the inhalation device.

16. The method of claim 10, wherein the second end portion of the body includes a hinge that joins the upper portion of the body to the lower portion of the body.

17. The method of claim 10, wherein:
the chamber is a first chamber and the dry powder drug is a first dry powder drug;
the lower portion of the body defines a second chamber containing a second dry powder drug, the exit channel fluidically coupled to the second chamber via the exit opening; and
the inhaling on the mouthpiece produces a flow of intake air within the second chamber to disaggregate the second dry powder drug, the disaggregated second dry powder drug exiting the inhalation device via the exit channel.

18. The method of claim 10, wherein the lower portion includes a raised section extending from an inner surface of the chamber, the raised section configured to guide a flow of the dry powder drug within the chamber.

* * * * *